(12) United States Patent  
Numajiri

(10) Patent No.: US 9,072,424 B2  
(45) Date of Patent: Jul. 7, 2015

(54) OPHTHALMOLOGIC APPARATUS AND CONTROL METHOD THEREFOR

(71) Applicant: CANON KABUSHIKI KAISHA, Tokyo (JP)

(72) Inventor: Yasuyuki Numajiri, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 89 days.

(21) Appl. No.: 13/970,533

(22) Filed: Aug. 19, 2013

(65) Prior Publication Data

US 2014/0063465 A1 Mar. 6, 2014

(30) Foreign Application Priority Data

Aug. 30, 2012 (JP) ................. 2012-189823

(51) Int. Cl.  
*A61B 3/10* (2006.01)  
*A61B 3/00* (2006.01)

(52) U.S. Cl.  
CPC ............. *A61B 3/0008* (2013.01); *A61B 3/0091* (2013.01); *A61B 3/1025* (2013.01)

(58) Field of Classification Search  
CPC .... A61B 3/102; A61B 3/1025; A61B 3/0091; A61B 3/15; A61B 2017/00057; A61B 2019/5234; A61B 3/0008

USPC .......................... 351/221, 246, 206, 205, 211  
See application file for complete search history.

(56) References Cited

U.S. PATENT DOCUMENTS

2007/0296919 A1*  12/2007  Hideshima et al. ........... 351/221

FOREIGN PATENT DOCUMENTS

JP          2000-201896 A      7/2000  
JP             4164411 B       10/2008

* cited by examiner

*Primary Examiner* — Hung Dang  
(74) *Attorney, Agent, or Firm* — Carter, DeLuca, Farrell & Schmidt, LLP

(57) ABSTRACT

To avoid, with a simple configuration and easy scanning, blocking of illumination light due to an eyelash or an eyelid of a subject, provided is an ophthalmologic apparatus, including: an optical system for scanning illumination light on an eye to be inspected in an up and down direction; a fixation target indicating unit for indicating a fixation target to the eye to be inspected at a selected position; a deflecting unit for changing an angle of the scanning for the eye to be inspected in a downward direction; and a fixation position shifting unit for shifting an indication position of the fixation target in a downward direction in accordance with the changed angle.

11 Claims, 7 Drawing Sheets

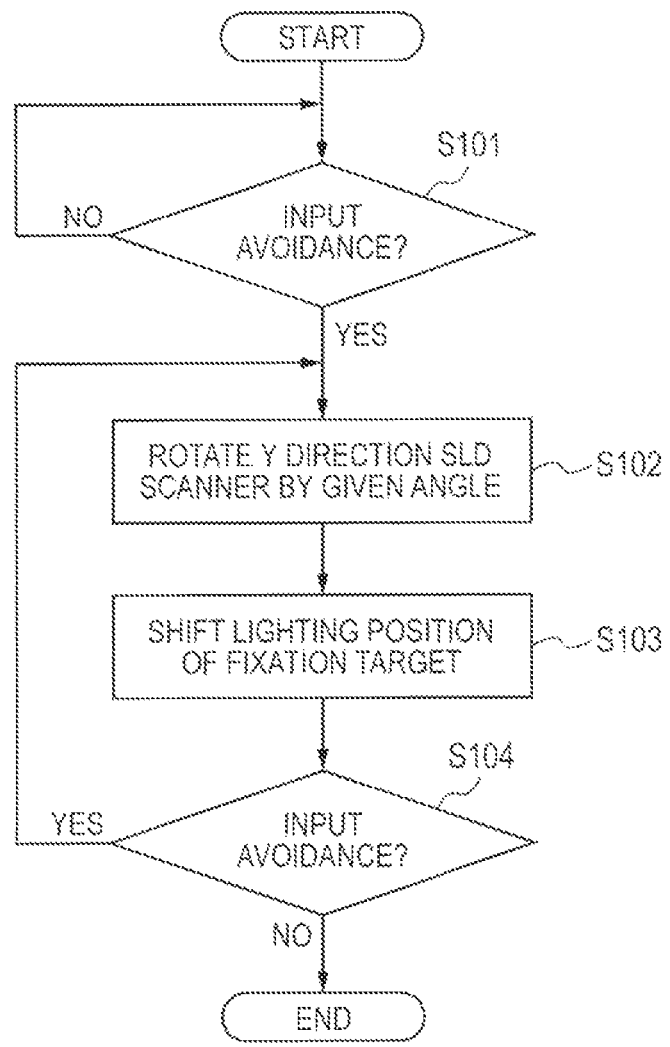

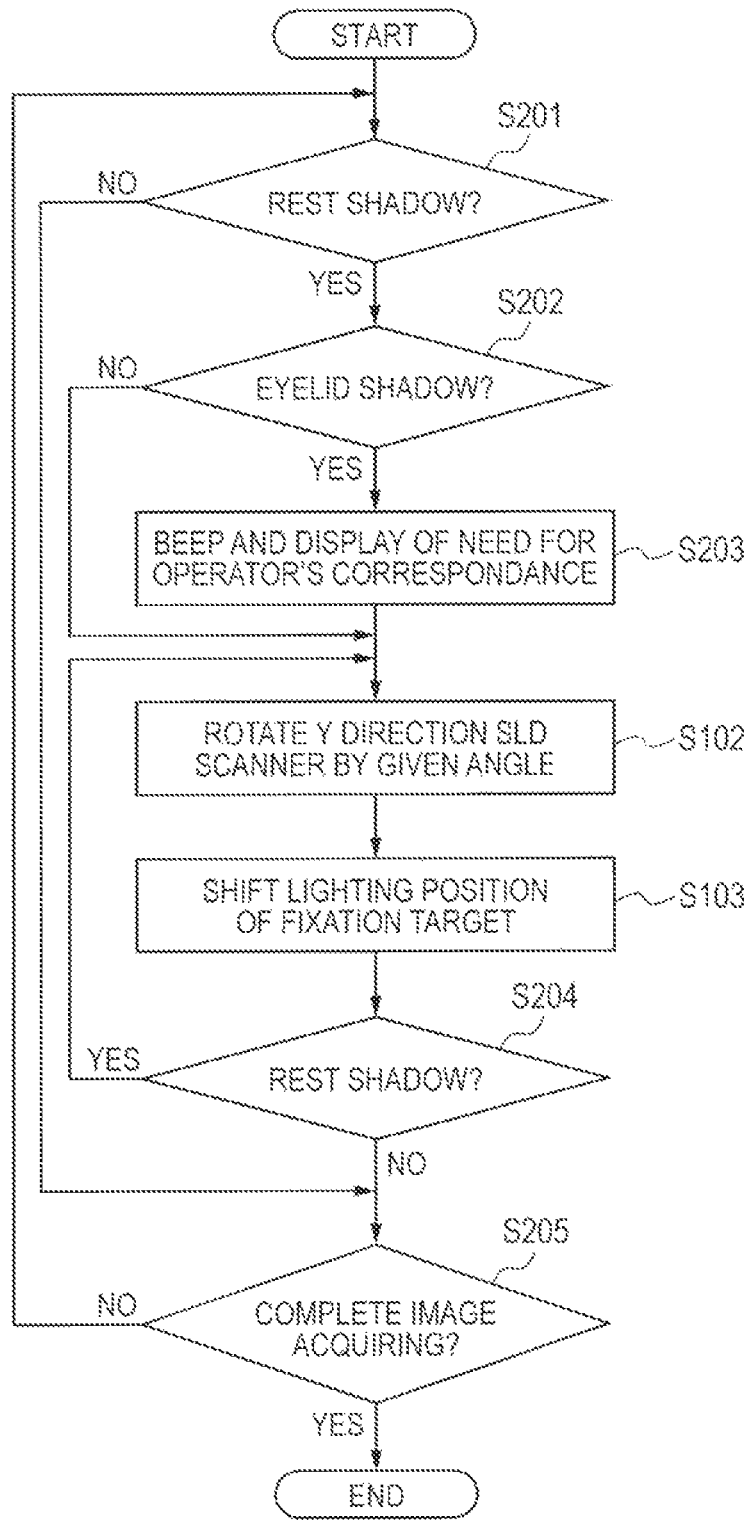

OPHTHALMOLOGIC APPARATUS AND CONTROL METHOD THEREFOR

BACKGROUND OF THE INVENTION

1. Field of the Invention

The present invention relates to an ophthalmologic apparatus and a control method therefor, and more particularly, to an ophthalmologic apparatus and a control method therefor, which are configured to reduce influence of an eyelash and an eyelid of an eye to be inspected at the time of picking up an image or measuring the eye.

2. Description of the Related Art

In recent years, as an apparatus for picking up an image of an eye, there has often been used an ocular image pickup apparatus which picks up an image of the eye by scanning the eye with illumination light, such as an optical coherence tomography (OCT) capable of acquiring a three-dimensional image, and a confocal scanning laser ophthalmoscope (SLO) for acquiring a high resolution moving image. In such an ocular image pickup apparatus, the eye is scanned with point or linear illumination light, and hence a part of the illumination light in the scanning operation may be blocked by an eyelash or an eyelid of the eye to be inspected. In this case, a part of the image cannot be formed, and hence the image pickup operation needs to be carried out again or the operator needs to open the eyelid or the subject, which imposes burdens on both the operator and the subject.

As a method of avoiding the blocking of the illumination light due to the eyelash or the eyelid, Japanese Patent No. 4,164,411 discloses the following method. That is, two light sources are provided in an up and down direction, and when light emitted from the lower light source is blocked by the eyelash or she eyelid, the upper light source is turned ON to illuminate the eye to be inspected with illumination light from a slightly lower side thereof. Further, Japanese Patent Application Laid-Open No. 2000-201896 discloses the following method. That is, a chin rest section of a face rest for fixing a face of the subject is moved toward an apparatus main body side to orient the face of the subject slightly upward. In this state, the eye is illuminated with illumination light from a slightly lower side thereof.

However, the configuration disclosed in Japanese Patent No. 4,164,411 requires an additional light source. Further, the configuration disclosed in Japanese Patent Application Laid-Open No. 2000-201896 requires an additional mechanism for the face rest, and the operation is cumbersome.

SUMMARY OF THE INVENTION

The present invention has an object to provide an ophthalmologic apparatus configured to perform a scanning operation with illumination light, which is capable of reducing influence of blocking of the illumination light due to an eyelash and an eyelid through a simple operation without using an additional optical system or mechanism.

In order to solve the above-mentioned problems, according to one aspect of the present invention, there is provided an ophthalmologic apparatus, including: an optical system for scanning illumination light on an eye to be inspected in an up and down direction; a fixation target indicating unit for indicating a fixation target to the eye to be inspected at a selected position; a deflecting unit for changing an angle of a center position of the scanning for the eye to be inspected; and a fixation position shifting unit for shifting an indication position of the fixation target in accordance with the changed angle.

Further, according to one embodiment, of the present invention, there is provided a control method for an ophthalmologic apparatus that includes an optical system for scanning illumination light on an eye to be inspected in an up and down direction, the control method including; indicating a fixation target by a fixation target indicating unit; receiving reflected and scattered light from the eye to be inspected, by scanning the illumination light on the eye to be inspected under a state in which the fixation target is indicated; changing an angle of a center position of the scanning for the illumination light on the eye to be inspected; and shifting an indication position of the fixation target by a shift amount determined in accordance with the changed angle.

According so one aspect of the present invention, it is possible to provide the ophthalmologic apparatus configured to perform the scanning operation with the illumination light, which is capable of reducing the influence of tine blocking of the illumination light due to the eyelash and the eyelid through the simple operation without using the additional optical system or mechanism.

Further features of the present invention will become apparent from the following description of exemplary embodiments with reference to the attached drawings.

BRIEF DESCRIPTION OF THE DRAWINGS

FIG. 5 is a slow chart illustrating an example of a flow according to the first embodiment.

FIG. 6 is a flow chart illustrating an example of a flow according to a second embodiment of the present invention.

DESCRIPTION OF THE EMBODIMENTS

Embodiments of the present invention are described in detail with reference to the attached drawings

First Embodiment

Figure 1:
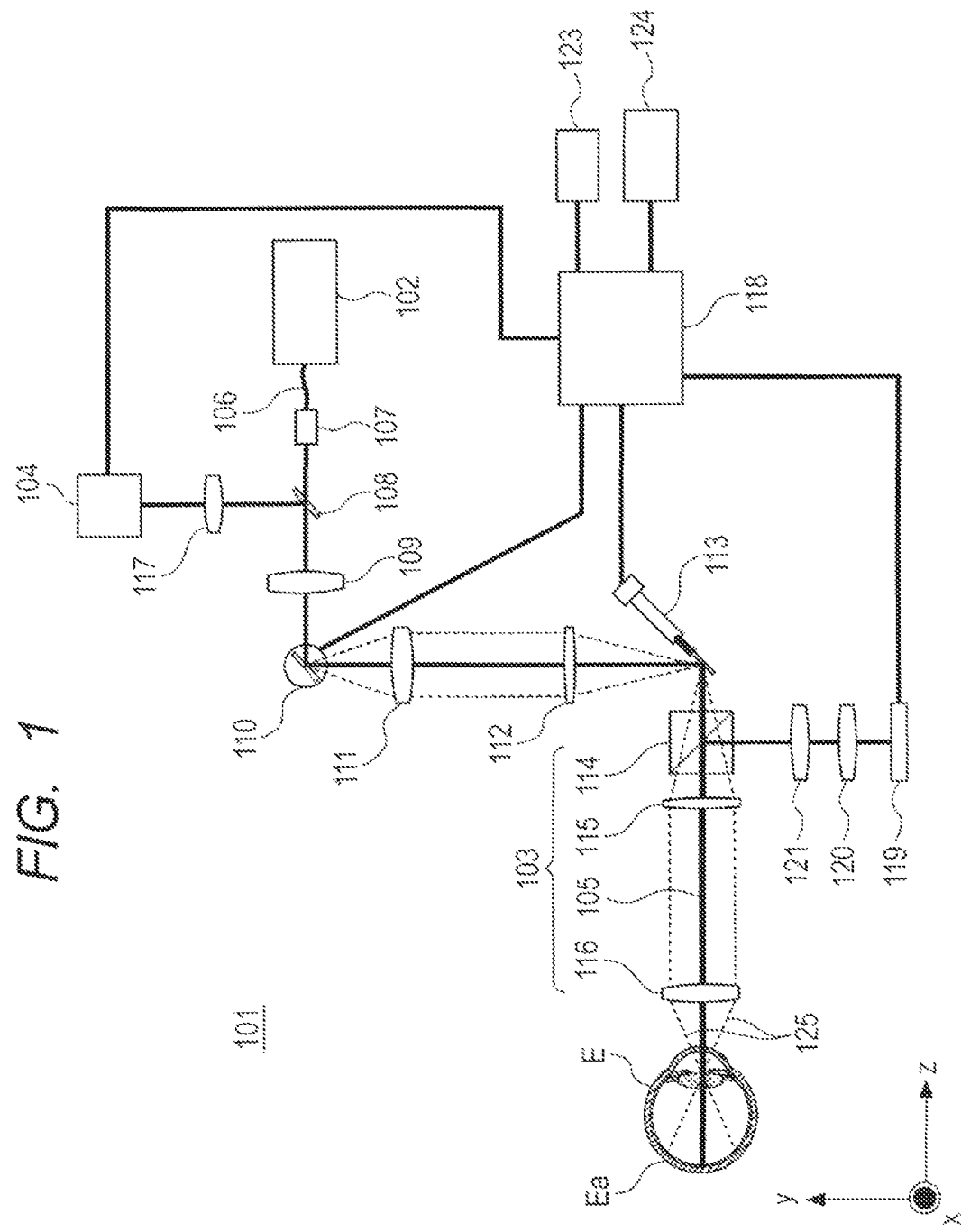
FIG. 1 is a diagram illustrating an example of a configuration of a fundus image pickup apparatus according to a first embodiment of the present indention.

A configuration of an ophthalmologic apparatus according to a first embodiment of the present invention is described with reference to FIG. 1.

This embodiment employs a general SLO apparatus configured to perform a scanning operation by illuminating a fundus with a point beam. An SLO apparatus 101 illuminates a fundus Ea of an eye E to be inspected with illumination light emitted from a light source 102 through an ocular optical system 103. Then, an image of reflected and scattered light as return light from the fundus Ea is formed on a light intensity sensor 104 through the ocular optical system 103, to thereby acquire a fundus image. Note that, an optical axis 105 is an optical axis of the ocular optical system 103, and in FIG. 1, a direction along the optical axis 105 corresponds to a z-axis, a direction perpendicular to the z-axis within a plane of the drawing sheet corresponds to a y-axis, and a direction perpendicular to the plane of the drawing sheet corresponds to an x-axis. In addition, the eye E to be inspected in FIG. 1 is viewed from one side, and the y-axis corresponds to an up and down direction of the eye E to be inspected, while the x-axis corresponds to a left and right direction of the eye E to be inspected.

As the light, source 102, a semiconductor laser or a super luminescent diode (SLD) light source may be suitable for use. As for the wavelength to be used, in order to reduce glare for a subject and maintain the resolution at the time of fundus observation, for example, a near-infrared wavelength region ranging from 700 nm to 1,000 nm is suitable for use. In this embodiment, a semiconductor laser having a wavelength of 780 nm is used as an example of the light source 102. The laser light emitted from the light source 102 propagates in a fiber 106 and exits from a fiber collimator 107 as a collimated light beam. The exiting beam passes through a perforated mirror 108, a lens 108, a Y direction SLO scanner 110, and relay lenses 111 and 112 so as to be guided to an X direction SLO scanner 113. Further, the beam passes through a beam splitter 114, a scan lens 115, and an ocular lens 116 of the ocular optical system 103 so as to enter the eye E to be inspected. Here, a resonant scanner is used for the X direction SLO scanner 113, and a galvano scanner is used for the Y direction SLO scanner 110. In addition, a direction of rotating the X direction SLO scanner 113 is a main scanning direction of the SLO, and a direction of rotating the Y direction SLO scanner 110 is a sub-scanning direction of the SLO.

The beam having entered the eye E to be inspected illuminates the fundus Ea of the eye E to be inspected as a point beam. This beam is reflected or scattered by the fundus Ea, propagates as reflected and scattered light along the same optical path, and returns to the perforated mirror 108, Among the reflected and scattered light rays, which are reflected or scattered by the fundus Ea, light rays passing through a peripheral portion of a pupil are reflected by the perforated, mirror 108, pass through a lens 117, and are received by the light intensity sensor 104 formed of an avalanche photodiode. Information of intensity detected by the light intensity sensor 104 is transmitted to a control portion 118 and is processed so that the fundus image is generated.

Figure 2A:
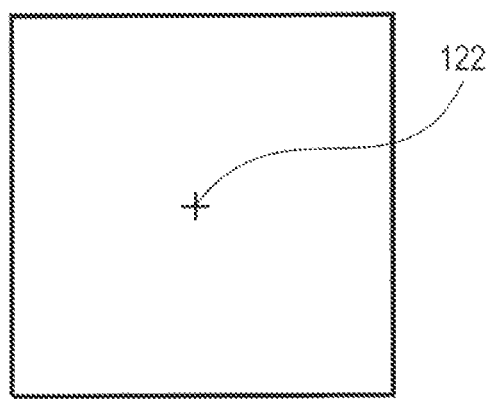
FIGS. 2A and 2B are diagrams illustrating an example of a fixation lamp according to the first embodiment.
Figure 2B:
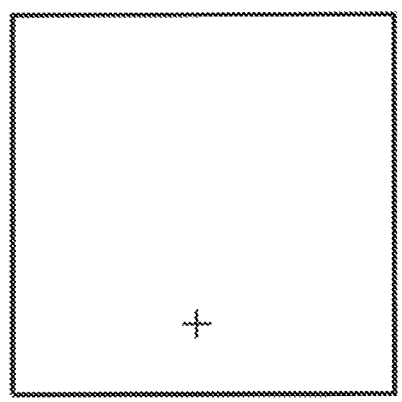

A fixation lamp 119 is configured to guide fixation by indicating a fixation target to the eye E to be inspected, and serves as a fixation target indicating unit. A light beam emitted from the fixation lamp 119 is reflected, by the beam splitter 114 through lenses 120 and 121, and passes through the scan lens 115 and the ocular lens 116 so as to enter the eye E to be inspected. In this embodiment, an organic electroluminescence (EL) element that is a light-emitting display module is used as an example of the fixation lamp 119. The fixation lamp 119 has 123×128 pixels, and as illustrated in FIG. 2A, lights and indicates the fixation target into a cross pattern 122. When necessary, as illustrated in FIG. 2B, an arbitrary position within a display area may be selected to light the fixation target at the selected position. In addition, liquid, crystal and a light emitting diode (LED) array may be used for the fixation lamp 119. That is, the fixation lamp 119 is not limited, to the organic EL element, and a different method may be used, instead. Further, the fixation target is not limited to the cross pattern, and a different snaps may be used instead.

The control portion 118 is connected to, in addition to the light intensity sensor 104, the Y direction SLO scanner 110, the X direction SLO scanner 113, the fixation lamp 119, an input device 123 for the operator to perform an input operation, and a monitor 124 for displaying the generated fundus image and an indication for the input operation.

When the control portion 118 controls the X direction SLO scanner 113 and the Y direction SLO scanner 110 to rotate by very small angles, the illumination beam scans the fundus Ea so that a two-dimensional fundus image is acquired. The control portion 116 controls the monitor 124 to display the fundus image. The inner region of two broken lines 125 in FIG. 1 corresponds to a scanning range of the illumination beam.

Figure 3A:
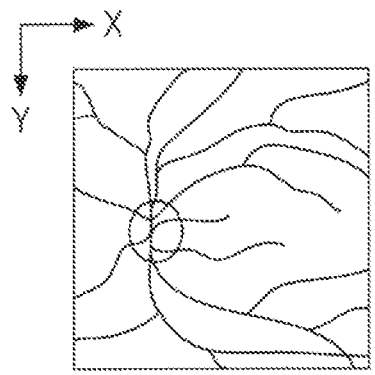
FIGS. 3A, 3B, and 3C are diagrams illustrating examples of a fundus image according to the first embodiment.
Figure 3B:
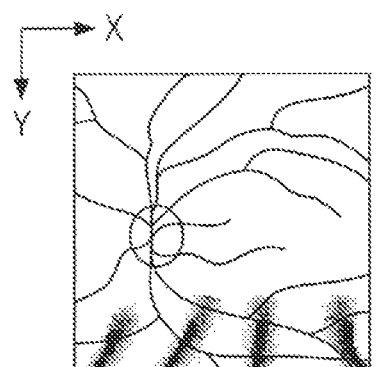
Figure 3C:
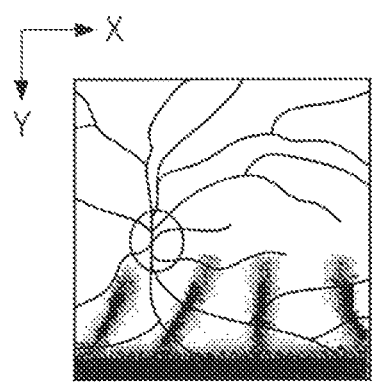
Figure 4A:
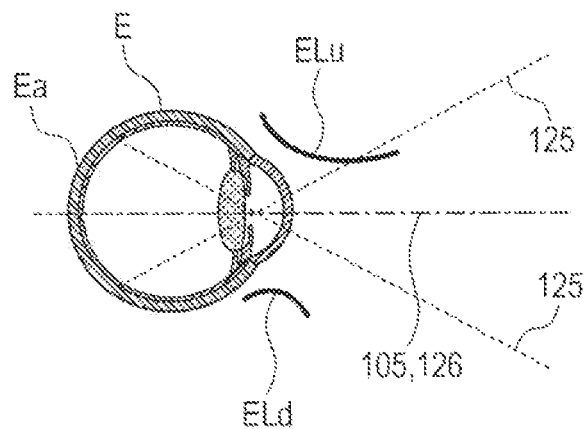
FIGS. 4A and 4B are explanatory diagrams illustrating an example of a sequence of a procedure according to the first embodiment.

FIG. 3A illustrates an example or the fundus image obtained in the configuration described above. When obtaining the fundus image, as illustrated in FIG. 4A, a part of the illumination beam may be blocked by an upper eyelash ELu of the eye E to be inspected. In the fundus image obtained at this time, as illustrated in FIG. 3B, blurred black lines generated by blocking the illumination beam due to the eyelash are observed at a lower portion of the image. Further, when a part of the illumination beam is blocked by an eyelid, as illustrated in FIG. 3C, a continuous black portion is observed below the black lines that are generated by blocking the illumination beam due to the eyelash. Note that, a lower eyelash ELd extends downward along the skin and is short in length so that the illumination beam is not blocked by the lower eyelash ELd. In this case, coordinate axes X and Y are set for the fundus image, and the X-axis and the Y-axis are parallel to the x-axis and the y-axis of FIG. 1, respectively, but the position of the origin is different from that of the x-axis and the y-axis of FIG. 1.

The operator activates the SLO apparatus 101, and aligns the position thereof with the eye E to be inspected to start picking up an image. Then, the control portion 113 controls the X direction SLO scanner 113 to repeatedly rotate by a very small angle so as to scan the illumination light on the eye E to be inspected in the main scanning direction. In synchronization with this scanning operation, the control portion 113 controls the Y direction SLO scanner 110 to rotate by a very small angle so as to scan the illumination light on the eye E to be inspected in the sub-scanning direction. The control portion 118 controls the monitor 124 to display a two-dimensional fundus image. Then, the control portion 113 repeatedly controls the scanning operation in the sub-scanning direction, that is, controls the Y direction SLO scanner 110 to rotate by a very small angle so that the fundus image is displayed on the monitor 124 as a real-time image.

Next, a procedure of reducing influence of the eyelash and the eyelid of the eye to be inspected according to this embodiment is described with reference to a flow chart of FIG. 5.

First, the operator views a real-time fundus image on the monitor 124, which is obtained under a state in which the subject stares at the fixation target indicated by the fixation lamp 119. When the blocking of the illumination beam due to the eyelash or the eyelid as illustrated in FIG. 3B or 3C is observed, the operator first prompts the subject to open the eye widely. When the illumination beam is still blocked, however, the operator inputs an instruction for avoidance by using the input device 123. In Step S101, the control portion 118 determines whether or not the operator has input the instruction tor avoidance. When the operator has not input the instruction for avoidance, the control portion 118 repeats the determination to wait for the input while maintaining the state in which the fixation target is indicated. When the operator has input the instruction for avoidance, in Step S102, the control portion 118 controls a scanning center position of the Y direction SLO scanner 110 to rotate by a predetermined angle, for example, 0.05° in this embodiment, to thereby illuminate the eye E to foe inspected with the illumination light from a slightly lover side. As illustrated in FIG. 4A, the scanning operation is designed so that the illumination light constantly passes through a point (pivot) inside the eye E to be inspected, and the illumination light passes through the pivot even when the eye E to be inspected is illuminated with the illumination light from the slightly lower side. In this embodiment, for example, the pivot is a point located 3 mm behind a vertex of a cornea on an axis of the eye. As described above, the Y direction SLO scanner 110 serves as a deflecting unit for changing the angle of the scanning for the eye to be inspected in a downward direction.

Then, in Step S103, the control portion 118 controls a lighting position of the fixation lamp 119 to shift by a n amount corresponding to the rotation angle, which is set for shifting a scanning start position, of the Y direction SLO scanner 110 in Step S102, so that a line of sight of the eye E to be inspected rotates downward. The shift amount may be calculated based on a magnification factor of the ocular optical system 103, a magnification factor of the fixation lamp 119, and a pitch of the pixels of the fixation lamp 119. In the example of this embodiment, the shift amount corresponds to two pixels. The control portion 118 serves as a fixation positron shifting unit. Through the shift of the lighting position, of the fixation lamp 119, the illumination position of the fundus Ea with the illumination light, that is, the image pickup position of the fundus image to be displayed on the monitor 124 is the same or substantially the same as that before the operator inputs the instruction for avoidance by using the input device 123.

Figure 4B:
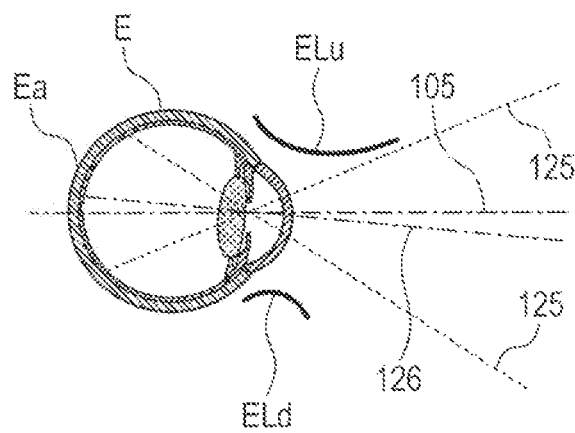

The operator views the real-time fundus image on the monitor 124, and continues to input the instruction for avoidance until the illumination beam, is no longer blocked by the eyelash or the eyelid. Note that, also in the second or subsequent input of the instruction for avoidance, the shift angle for the scanning center position may be set to 0.05° similarly to the first input of the instruction for avoidance, but the shift angle may be changed to a gradually smaller value in the second or subsequent input. For example, in the second input, of the instruction for avoidance, the shift angle may be set to 0.04°. With this setting, fine adjustment may be performed. In Step S104, the control portion 118 determines whether or not the operator has input the instruction, for avoidance again. When the operator has input the instruction for avoidance, the control, portion 118 continues controlling the Y direction SLO scanner 110 to rotate in Step S102 and the lighting position of the fixation lamp 113 to shift in Step S103. When the operator no longer inputs the instruction for avoidance in Step S104, the control portion 118 ends the procedure. When the illumination beam is no longer blocked by the eyelash or the eyelid, the relationship among the eye E to be inspected, the upper eyelash Elu, and the illumination beam is as illustrated in FIG. 4B, Note that, in FIG. 4A, the optical axis 105 is the optical axis of the ocular optical system 103, the inner region of the two broken lines 125 corresponds to the scanning range of the illumination beam, and a scanning center 126 is located within the scanning range. In FIG. 4A, the optical axis 105 matches with the scanning center 126. In FIG. 4B, on the other hand, the position of the optical axis 105 is the same as that in FIG. 4A, while the scanning center 126 is rotated by an amount corresponding to the repeated rotation of the scanning center position of the Y direction SLO scanner 110 by the predetermined angle in Step S102. Further, the line of sight (not shown) of the eye E to be inspected is rotated by an amount corresponding to the repeated shift of the lighting position of the fixation lamp 119 in Step S103.

At the time of the rotation described above, the position of the pivot is different from the position of the rotation center of the eye E to be inspected (that is generally located 13 mm behind the vertex of the cornea on the axis of the eye), and hence the illumination position of a pupil with the illumination light is different. There arises no problem when the rotation angle is small and the illumination light passes through the pupil without being blocked by an iris, but the illumination light may be blocked by the iris when, the rotation angle is large.

In this case, it is only necessary to perform again the positional alignment between the eye E to be inspected and the SLO apparatus 101, which is constantly performed, before the eye inspection at a preparation stage of the eye inspection. In this embodiment, the height of an abutment member, on which the subject brings his/her chin into abutment so as to fix the position of the face to the apparatus at the time of the eye inspection, is changed relative to the height of the optical system of the SLO apparatus 101. In this manner, the illumination light, passes through the pupil without being blocked by the iris. Thus, the image pickup operation or measurement of the eye E to be inspected may be carried cut in a proper manner. Note that, the shift angle for the scanning center position of the Y direction SLO scanner 110 is not limited to 0.05°, and may be set to a different value. Further, the height of the SLO apparatus 101 may be changed so as to change the height of the eye E to be inspected relative to the height or the optical system of the SLO apparatus 101.

Note that, there may be employed a method that Involves moving the scanning center position of the Y direction SLO scanner 110 at one time, confirming that the illumination beam is no longer blocked by the eyelash or the eyelid, and then shifting the lighting position of the fixation lamp 119 at one time. However, the subject may lose sight of the cross pattern 122 and the face may move when the eye moves widely, and hence it is preferred that the scanning center position of the Y direction SLO scanner 110 be gradually shifted as described above.

The operator continues to pick up an image of the fundus Ea by using the SLO apparatus 101 as necessary. When the illumination beam is blocked by the eyelash or the eyelid again, the operator only needs to input the instruction for avoidance by using the input device 123 again, to thereby avoid the blocking of the illumination beam.

As described above, in this embodiment, it is possible to reduce the influence of the blocking of the illumination light due to the eyelash and the eyelid through the simple operation without using the additional optical system or mechanism.

Second Embodiment

In a second embodiment of the present invention, the blocking of the illumination beam due to the eyelash or the eyelid is detected automatically. The configuration of the ophthalmologic apparatus is the same as that of the first embodiment illustrated in FIG. 1, and description of the configuration of the ophthalmologic apparatus is therefore omitted herein.

Similarly to the first embodiment, the operator activates the SLO apparatus 101, and aligns she position thereof with the eye E to be inspected to start picking up an image. Further, similarly to the first embodiment, the control portion 118 controls the X direction SLO scanner 113 and the Y direction SLO scanner 110 to scan the illumination light on the eye E to be inspected, and controls the monitor 124 to display a two-dimensional fundus image. Then, the control portion 118 repeatedly controls the Y direction SLO scanner 110 to rotate by a very small angle so that the fundus image is displayed on the monitor 124 as a real-time image.

Figure 7A:
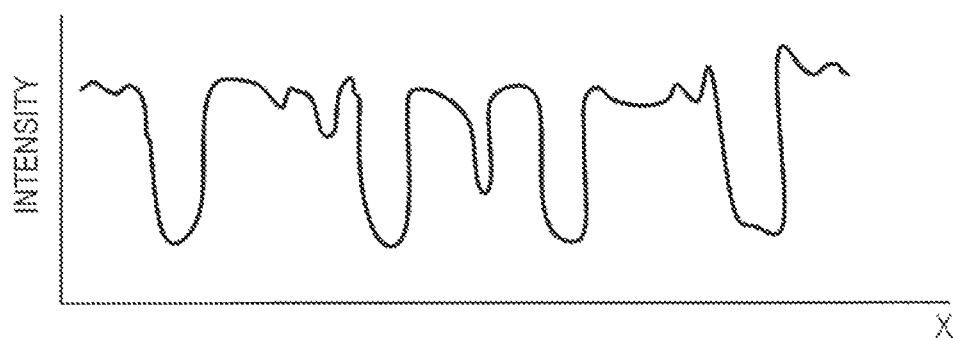
FIGS. 7A and 7B are graphs showing an example of automatic determination according to the second embodiment.
Figure 7B:
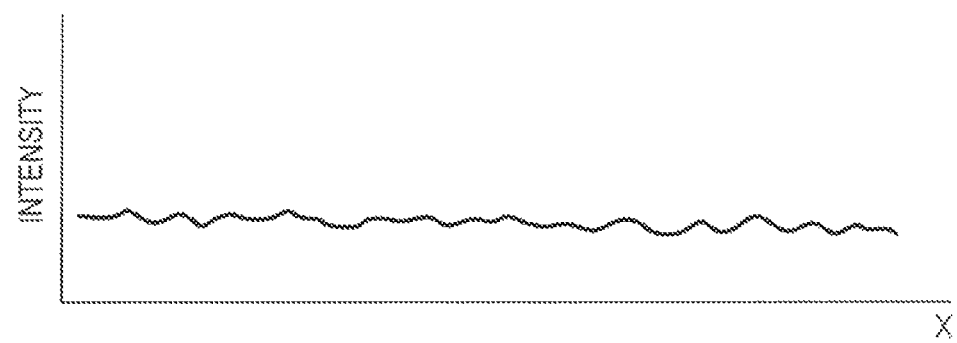

A procedure of reducing the influence of the eyelash and the eyelid of the eye to be inspected according to this embodiment is described with reference to a flow chart of FIG. 6. In Step S201, the control portion 118 determines whether or not the fundus image shows a shadow that is caused by blocking the illumination beam due to the eyelash or the eyelid of the eye to be inspected. The SLO apparatus 101 rotates the X direction SLO scanner 113 in a reciprocating manner to repeatedly scan the illumination light on the eye E to be inspected at high speed in the main scanning direction, and rotates in this state the Y direction SLO scanner 110 to gradually scan the illumination light on the eye E to be respected in the sub-scanning direction, thereby obtaining a single fundus image. When the main scanning operation is performed once to scan a portion of the black lines generated by blocking the illumination beam due to the eyelash as indicated in the lower part of FIG. 8B, the intensity information obtained by the light intensity sensor 104 at this time repeatedly indicates, as shown in FIG. 7A, dark portions that are at least several times as wide as thick blood vessels indicated by the intensity signal. Further, when the main scanning operation is performed once to scan the black portion generated by blocking the illumination beam due to the eyelid as indicated in the lowest part of FIG. 3C, the intensity information obtained by the light intensity sensor 104 indicates, as shown in FIG. 7B, only dark portions in the entire range. Thus, based on the intensity information obtained by the light intensity sensor 104, the control portion 118 may easily determine whether or not the fundus image shows a shadow that is caused by blocking the illumination beam due to the eyelash or the eyelid. In this case, the control portion 116 serves as a determination unit for determining the presence and absence of the blocking of the illumination light due to the eyelid or the eyelash of the eye to be inspected. When the illumination light is not blocked, the control portion 118 proceeds to Step S205, and determines whether or not the operator has input an instruction to complete the image acquiring by using the input device 123. When the operator has input the instruction to complete the image acquiring, the control portion 118 completes the image acquiring. When the operator has not input the instruction to complete the image acquiring, the control portion 118 returns to Step S201. Note that, in a case of a blink of the eye, the entire fundus image becomes black, and hence the blink of the eye may be distinguished easily, When the illumination beam is blocked in Step S201, in Step S202 subsequent to Step S201, the control portion 118 determines, by the method described above, whether or not the illumination beam is blocked by the eyelid. When it is determined that the illumination beam is blocked by the eyelid, in Step S203, the control portion. 118 controls an informing unit such as a sound generator (not shown) to generate a beeping sound so as to inform the operator of the state in which the illumination beam, is blocked by the eyelid, and controls the monitor 124 to display an indication, so that the operator prompts the subject to open the eye widely. The sound generator or the monitor 124 serves as an attention unit for attracting attention of the subject or the operator. Then, as in the first embodiment, the control portion 118 proceeds to Step S102, and controls the scanning center position of the Y direction SLO scanner 110 to rotate by a predetermined angle, for example, 0.05° in this embodiment, to thereby illuminate the eye E to be inspected with the illumination light from a relatively lower side. Subsequently, similarly to the first embodiment, in Step S103, the control portion 118 controls the lighting position of the fixation lamp 113 to shift by an amount cot responding to the rotation of the Y direction SLO scanner 110, which is performed in Step S102, so that the line of sight of the eye E to be inspected rotates downward. In this case, the control portion 118 serves also as an angle changing unit for changing the angle of scanning the eye to be inspected in a downward direction so as to shift the indication position of the fixation target in a downward direction in accordance with the changed angle. Note that, the shift angle for the scanning center position of the Y direction SLO scanner 110 is not limited to 0.05°, and may be set to a different value.

In Step S204 subsequent to Step S103, the control portion 118 determines whether or not the illumination beam is still blocked by the eyelash or the eyelid of the eye to be inspected. When the illumination beam is still blocked, the control portion 118 repeats Step S102. When the illumination beam, is no longer blocked, the control portion 118 proceeds to Step S205.

As described above, in this embodiment, it is possible to automatically reduce the influence of the blocking of the illumination light due to the eyelash and the eyelid, without using the additional optical system or mechanism.

Other Embodiments

In the embodiments described above, the SLO apparatus is used, bur the present invention is not limited to the SLO apparatus as long as the apparatus is capable of observing the eye by scanning the eye with the illumination light in the op and down direction. Further, the SLO apparatus, an ophthalmologic apparatus such as an OCT apparatus, which is configured to exert a different function by scanning the eye with the illumination light in the up and down direction, and an ophthalmologic apparatus for carrying out, for example, a confrontation field rest or a blood flow measurement may be used in combination so as to observe the blocking of the illumination light due to the eyelash or she eyelid based on an image obtained by the SLO apparatus. In this case, it is desired that the scanning angle be equal to or smaller than the scanning angle of the SLO apparatus.

Note that, the embodiments described above are mainly directed to the case where the entrance of the measuring light into the eye to be inspected is prevented by the upper eyelash, but the present invention is not limited thereto. For example, it is understood that the present invention is also applicable to a case where the entrance of the measuring light into the eye to be inspected is prevented, by the lower eyelash.

Further, the present invention is also implemented by executing the following process. Specifically, in this process, software (program) for implementing the functions of the above-mentioned embodiments is supplied to a system, or an apparatus via a network or various kinds of storage medium, and a computer (CPU, MPU, or the like) of the system or the apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-183823, filed Aug. 30, 2012, which is hereby incorporated by reference herein in its entirety.

What is claimed is:
1. An ophthalmologic apparatus, comprising:
an optical system tor scanning illumination light on an eye to be inspected in an up and down direction;
a fixation target indicating unit for indicating a fixation target to the eye to be inspected at a selected position;

a deflecting unit for changing an angle of a center position of the scanning for the illumination light on the eye to be inspected; and a fixation position shifting unit for shifting an indication position of the fixation target in accordance with the changed angle.

2. An ophthalmologic apparatus according to claim 1, further comprising a determination unit for determining presence and absence of blocking of the illumination light due to one of an eyelid, and an eyelash of the eye to be inspected based on reflected and scattered light, which corresponds to the illumination light reflected and scattered from the eye to be inspected, wherein the deflecting unit is configured to change the angle based on the determination performed by the determination unit.

3. An ophthalmologic apparatus according to claim 2,
wherein the determination unit is configured to determine the presence and absence of the blocking of the illumination light based on intensity of she reflected and scattered light.

4. An ophthalmologic apparatus according to claim 2, wherein the determination unit is configured so determine whether or not the blocking of the illumination light is caused by the eyelid.

5. An ophthalmologic apparatus according to claim 4, further comprising an informing unit for informing an operator when the determination unit determines that the blocking of the illumination light is caused by the eyelid.

6. An ophthalmologic apparatus according to claim 1, wherein the angle of the center position of the scanning is changed in a downward direction with respect to the eye to be inspected.

7. A control meshed for an ophthalmologic apparatus that comprises an optical system, for scanning illumination light on an eye to be inspected in an up and down direction, the control method comprising:

indicating a fixation target by a fixation target indicating unit;

receiving reflected and scattered light from the eye to be inspected by scanning the illumination light on the eye to be inspected under a state in which the fixation target is indicated;

changing an angle of a center position of the scanning for the illumination light on the eye to be inspected; and shifting an indication position of the fixation target by a shift amount determined in accordance with the changed angle.

8. A control method according to claim 7, further comprising determining presence and absence of blocking of the illumination light due to one of an eyelid and an eyelash of the eye to be inspected based on intensity of the reflected and scattered light, wherein she changing comprises changing the angle based on the determining.

9. A control method according to claim 8, wherein the determining comprises determining whether or not the blocking of the illumination light is caused by the eyelash based on presence and absence of repetition of a low-intensity portion of the reflected and scattered light.

10. A non-transitory tangible medium having recorded thereon a program for causing a computer to perform the steps of the control method for an ophthalmologic apparatus according to claim 7.

11. A control method according to claim 7, wherein the angle of the center position of the scanning is changed in a downward direction with respect to the eye to be inspected.

* * * * *